(12) United States Patent
Huchler et al.

(10) Patent No.: US 8,084,634 B2
(45) Date of Patent: Dec. 27, 2011

(54) PRODUCTION METHOD

(75) Inventors: Guenther Huchler, Hochdorf (DE); Werner Rall, Mittelbiberach (DE); Uwe Reis, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 18 days.

(21) Appl. No.: 12/710,605

(22) Filed: Feb. 23, 2010

(65) Prior Publication Data

US 2010/0152439 A1    Jun. 17, 2010

Related U.S. Application Data

(62) Division of application No. 11/840,397, filed on Aug. 17, 2007, now Pat. No. 7,696,346.

(30) Foreign Application Priority Data

Aug. 19, 2006    (DE) .................. 10 2006 039 038

(51) Int. Cl.
C07C 69/00 (2006.01)
C07C 69/76 (2006.01)
C07C 229/00 (2006.01)
(52) U.S. Cl. ............... 560/55; 560/106; 562/458
(58) Field of Classification Search ............. 562/458; 560/55, 106
See application file for complete search history.

(56) References Cited

U.S. PATENT DOCUMENTS

2008/0280887 A1    11/2008 Mueller et al.

FOREIGN PATENT DOCUMENTS

| CA | 2558889 A1 | 10/2005 |
| EP | 1310488 A1 | 5/2003 |
| EP | 1770087 A1 | 9/2005 |
| WO | 2005092880 A1 | 10/2005 |
| WO | 2008060568 A2 | 5/2008 |

OTHER PUBLICATIONS

Staab et al.; Syntheses Using Heterocyclic Amides (Azolides); Angew. Chem. Internat. Edit; 1962; vol. 1; No. 7; pp. 351-367.

Ting et al.; Synthesis of Substituted 4(Z)-(Methoxyimino)pentyl-1-piperidines as Dual NK1/NK2 Inhibitors; Bioorganic & Medicinal Chemistry Letters; 2001; vol. 11; pp. 491-494.

Borch et al.; Cyanohydridoborate anion as a selective reducing agent; Journal of the American Chemical Society; 1971; vol. 93; No. 12; pp. 2897-2904.

Dardonville; Synthesis and Analgesic Activity of a Series of New Azaalkane Bis-guanidinium and Bis(2-aminoimidazolinium) Compounds; Bioorganic and Medicinal Chemistry; 2003; vol. 11; pp. 1283-1291.

International Search Report, Form PCT/ISA/220, for corresponding PCT/EP2007/058526, dated Jan. 19, 2009.

*Primary Examiner* — Bruck Kifle
(74) *Attorney, Agent, or Firm* — Michael P. Morris; Alan R. Stempel

(57) ABSTRACT

The present invention relates to a process for preparing compounds of general formula I

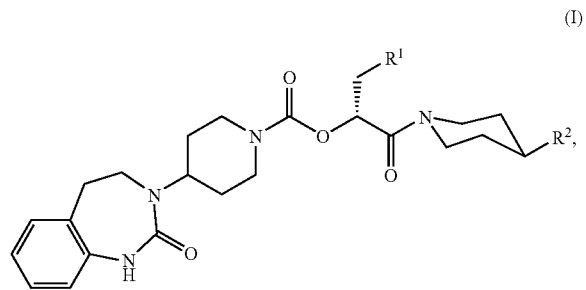

wherein $R^1$ and $R^2$ are defined as in claim 1, the pharmaceutically acceptable salts and the solvates thereof, which may be prepared starting from compounds of general formula II

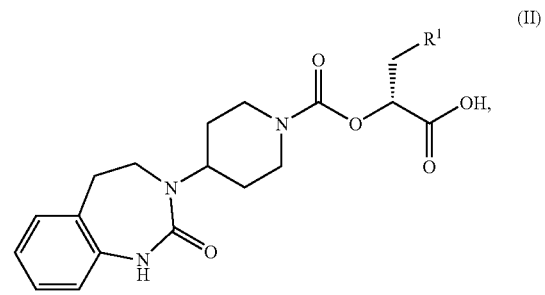

wherein $R^1$ is defined as in claim 1.

6 Claims, No Drawings

PRODUCTION METHOD

RELATED APPLICATIONS

This application is a division of U.S. application Ser. No. 11/840,397, filed on Aug. 17, 2007, which claims priority benefit, as does the present application, to DE102006039038, filed on Aug. 19, 2006.

The present invention relates to a process for preparing compounds of general formula I

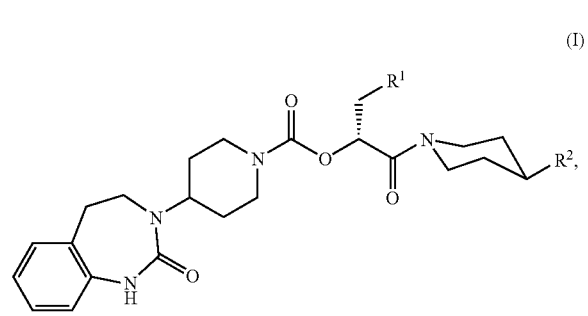

wherein $R^1$ and $R^2$ are as defined hereinbelow, the pharmaceutically acceptable salts and the solvates thereof, which can be prepared starting from compounds of general formula II

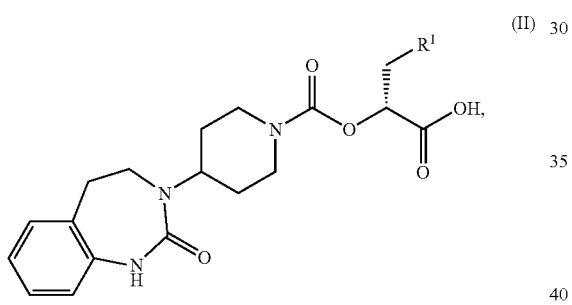

wherein $R^1$ is as defined hereinbelow.

BACKGROUND TO THE INVENTION

1. Technical Field

The present invention relates to a process for preparing compounds of general formula I, which is based on a stepwise synthesis starting from compounds of general formulae III and IV. In addition, the invention relates to the compounds of general formulae III and IV per se, as these are particularly suitable for preparing the compounds of general formula I which have CGRP-antagonistic properties.

2. Prior Art

International Patent Applications PCT/EP03/11762 and PCT/EP2005/003094 have already described compounds with CGRP-antagonistic properties as well as some laboratory synthesis methods for preparing small amounts.

In addition, a process for preparing 3-(4-piperidinyl)-2,3,4,5-tetrahydro-1,3-benzodiazepin-2(1H)-one is described in European Patent Application No. 04017424.5.

DETAILED DESCRIPTION OF THE INVENTION

The compounds of general formulae III and IV are valuable starting materials for the synthesis of the compounds of general formula I which have CGRP-antagonistic properties.

The isolated intermediate stages occur as crystalline solids, which is a major advantage for purification as well as for the separation of any mixtures of enantiomers that may occur.

The compounds of general formula II are valuable intermediate products for the synthesis of the compounds of general formula I which have CGRP-antagonistic properties.

In a first aspect the present invention relates to a process for preparing compounds of general formula II

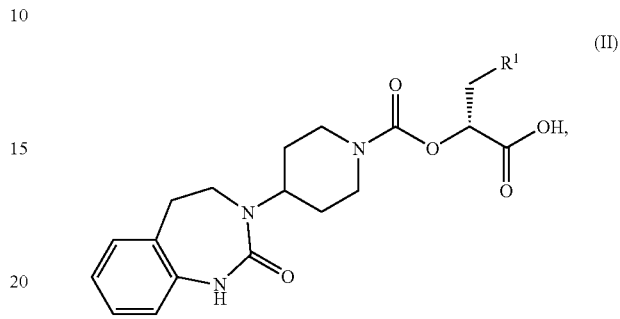

wherein
$R^1$ denotes a group

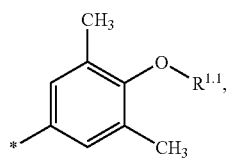

wherein
$R^{1.1}$ denotes H, $C_{1-3}$-alkyl, C(O)—O-benzyl, C(O)—O-tert.butyl or benzyl, preferably benzyl,
comprising the steps of:
(a) coupling a compound of general formula III

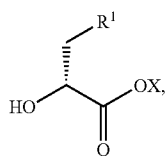

wherein $R^1$ is as hereinbefore defined and X denotes a hydrogen atom or a metal atom selected from among lithium, sodium and potassium, preferably sodium, or a hydrate thereof, to a compound of general formula IV

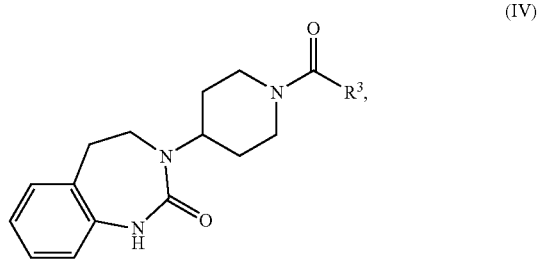

wherein R³ denotes an imidazole or triazole group, preferably an imidazole group, which is attached via a nitrogen atom;
(b) isolating a compound of general formula II obtained in step (a), preferably by crystallisation, from a solvent and
(c) optionally recrystallising a solid obtained in step (b) from a suitable solvent.

In the coupling in step (a) preferably 1.0 equivalents of a compound of general formula III are reacted with 1.1 to 1.5 equivalents, preferably with 1.1 equivalents, of a compound of general formula IV in a polar solvent in the presence of a strong base. The polar solvent used may be tert.-butanol or tetrahydrofuran or mixtures of these solvents, while mixtures in the ratio 1:1 are preferred. The solvent is preferably added in an amount of 1 to 3 mL/mmol of the compound used, preferably in an amount of 1 to 2 mL/mmol of the compound used.

The base is preferably added in an amount of 1.1 to 1.5 equivalents, preferably in an amount of 1.2 equivalents, based on the amount of the compound of general formula III used. It is possible to use potassium tert.butoxide, sodium tert.butoxide, lithium tert.butoxide or sodium tert.amylate, while potassium tert.butoxide is preferably used according to the invention.

The crystallisation in step (b) and the recrystallisation in step (c) are carried out independently of one another, preferably in a polar solvent. The polar solvent used may be, for example, water, ethanol, isopropanol or n-butyl acetate as well as mixtures of these solvents. According to the invention the crystallisation in step (b) is preferably carried out from a mixture of n-butyl acetate and water in the ratio 18:1 and the recrystallisation in step (c) is from a mixture of isopropanol and water in the ratio 20:1.

In a second aspect the present invention relates to a process for preparing compounds of general formula I

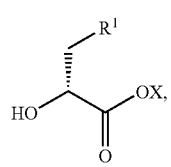
(I)

wherein
R¹ denotes a group

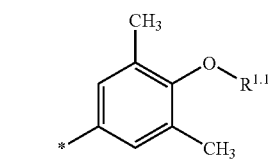

wherein
R$^{1.1}$ denotes H, C$_{1-3}$-alkyl, C(O)—O-benzyl, C(O)—O-tert.butyl or benzyl, preferably H or benzyl, and
R² denotes a secondary amine —NR$^{2.1}$R$^{2.2}$, wherein
R$^{2.1}$ and R$^{2.2}$ independently of one another may be selected from among C$_{1-3}$-alkyl and benzyl, or the group —NR$^{2.1}$R$^{2.2}$ together forms a cyclic amine which may be selected from among morpholin-4-yl, 1-methylpiperazin-4-yl, 1-benzylpiperazin-4-yl, 1-(C$_{1-3}$-alkylcarbonyl)-piperazin-4-yl, 1-(tert.butyloxycarbonyl)-piperazin-4-yl, 1-(benzyloxycarbonyl)-piperazin-4-yl, piperidin-1-yl and pyrrolidin-1-yl,
the salts and solvates thereof, comprising the steps of:
(a) coupling a compound of general formula III

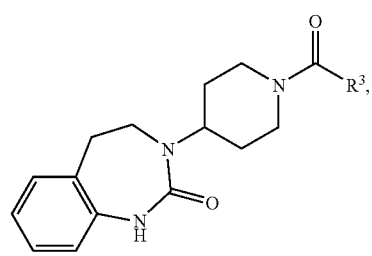
(III)

wherein R¹ is as hereinbefore defined and X denotes a hydrogen atom or a metal atom selected from among lithium, sodium and potassium, preferably sodium, or a hydrate thereof, to a compound of general formula IV

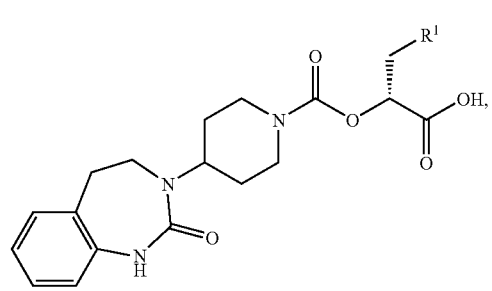
(IV)

wherein R³ denotes an imidazole or triazole group, preferably an imidazole group, which is attached via a nitrogen atom;
(b) reacting a product of general formula II obtained in step (a)

(II)

wherein R¹ is as hereinbefore defined, with a compound of general formula V

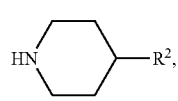
(V)

wherein R² is as hereinbefore defined; and
(c) in order to prepare compounds of general formula I wherein R$^{1.1}$ denotes a hydrogen atom, a protective group present is optionally subsequently cleaved from a compound of general formula I wherein $R^{1.1}$ denotes one of the groups C(O)—O-benzyl, C(O)—O-tert.butyl or benzyl.

In the coupling in step (a) preferably 1.0 equivalents of a compound of general formula II and 1.0 to 1.5 equivalents of a compound of general formula III are suspended in a polar solvent and reacted at elevated temperature in the presence of a strong base.

The polar solvent used may preferably be tert.butanol or THF. The base used may be selected from among potassium tert.butoxide, sodium tert.butoxide, lithium tert.butoxide and sodium tert.amylate. The reaction is preferably carried out at a temperature between 40 and 80° C.

The reaction described under step (b) above is preferably carried out at low temperature in the presence of an amine and a condensing agent in a polar, aprotic solvent.

The amine used may be selected from among triethylamine, diisopropylethylamine, ethyldiisopropylamine and tributylamine. The condensing agent may be selected from among propanephosphonic anhydride, dicyclohexylcarbodiimide, carbonyldiimidazole, carbonylditriazole, 2-(1H-benzotriazol-1-yl)-1,1,3,3-tetramethyluronium-tetrafluoroborate, 1-ethyl-3-(3'-dimethylamino-propyl)-carbodiimide and chlorodimethoxy-triazine, optionally in the presence of hydroxysuccinimide, hydroxybenzotriazole, p-nitrophenol or pentafluorophenol.

The polar aprotic solvent used may be THF or ethyl acetate. According to the invention the reaction is preferably carried out at a temperature between 0 and 25° C.

For the optional cleaving of a benzyl protective group in step (c), a compound of general formula I wherein $R^{1.1}$ denotes a benzyl group obtained in step (b), is dissolved in a polar solvent, such as for example methanol, ethanol, water, acetone, tetrahydrofuran, dimethylformamide or propanol, and hydrogenated in a pressurised reactor. The hydrogenation agent used may be Pd/C or Pd(OH)$_2$ for example. Advantageous conditions for the hydrogenation are temperatures of 40 to 80° C. and an excess hydrogen pressure of not more than 3 bar. After the catalyst has been filtered off the compound of general formula I wherein $R^{1.1}$ denotes a hydrogen atom may be obtained by concentrating the solvent with the addition of another polar solvent, preferably ethanol.

In a third aspect the present invention relates to the compounds of general formula III

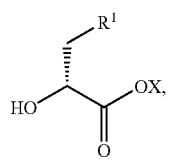

(III)

wherein
$R^1$ denotes a group

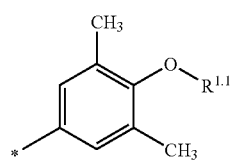

wherein
$R^{1.1}$ denotes H, $C_{1-3}$-alkyl, C(O)—O-benzyl, C(O)—O-tert.butyl or benzyl, preferably benzyl, and
X denotes a hydrogen atom or a metal atom selected from among lithium, sodium and potassium, preferably sodium, and the hydrates thereof.

A preferred third object includes the following compounds of formulae IIIa to IIId:

| No. | Structure |
|---|---|
| (1) | ![structure IIIa] (IIIa) |
| (2) | ![structure IIIb] (IIIb) |
| (3) | ![structure IIIc] (IIIc) |
| (4) | ![structure IIId] (IIId) |

-continued

| No. | Structure |
|---|---|
| (5) | 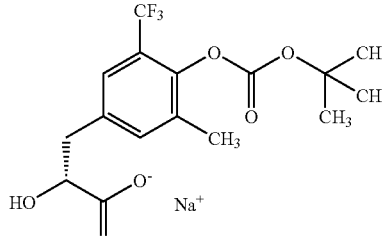 |

(IIIe)

and the hydrates thereof.

Another preferred third object relates to the compound (αR)-α-hydroxy-3,5-dimethyl-4-(phenylmethoxy)-phenyl-propionic acid monosodium salt of formula IIIa

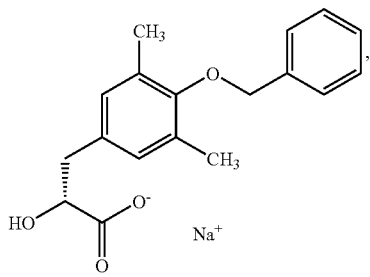

(IIIa)

which occurs in crystalline form and is characterised by a high degree of stability.

The crystalline compound of formula IIIa is characterised by a characteristic melting point of T=237±3° C. The value given was determined by Differential Scanning Calorimetry (DSC: evaluated by onset, heating rate: 10° C./min) (DSC 821 of Mettler Toledo).

Another preferred third object of the present invention relates to the crystalline compound of formula IIIa, characterised by a water content of between 0.5 and 3%.

In a fourth aspect the present invention relates to a process for preparing compounds of general formula III

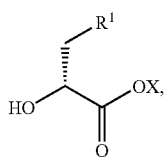

(III)

wherein
$R^1$ denotes a group

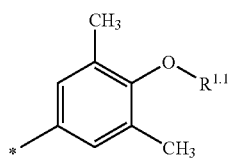

wherein
$R^{1.1}$ denotes H, $C_{1-3}$-alkyl, C(O)—O-benzyl, C(O)—O-tert.butyl or benzyl, preferably benzyl, and the hydrates thereof, and X denotes a hydrogen atom or a metal atom selected from among lithium, sodium and potassium, preferably sodium, characterised in that (a) (diethoxyphosphinyl)-hydroxyacetic acid is reacted with cyclohexane dimethylketal and optionally in the presence of an acid in a non-polar aprotic solvent and the diethyl (3-oxo-1,4-dioxaspiro[4.5]dec-2-yl)-phosphonate is obtained by azeotropic distillation of the methanol released;

(b) the diethyl (3-oxo-1,4-dioxaspiro[4.5]dec-2-yl)phosphonate obtained under (a) is reacted in the presence of lithium chloride and a strong base with a compound of general formula VI

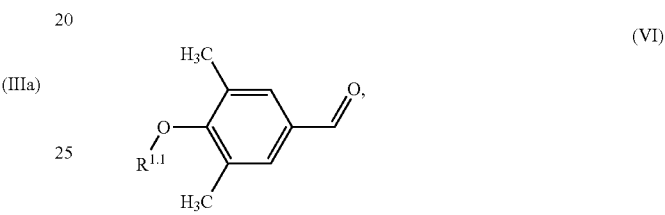

(VI)

wherein $R^{1.1}$ is as hereinbefore defined, and a compound of general formula VII

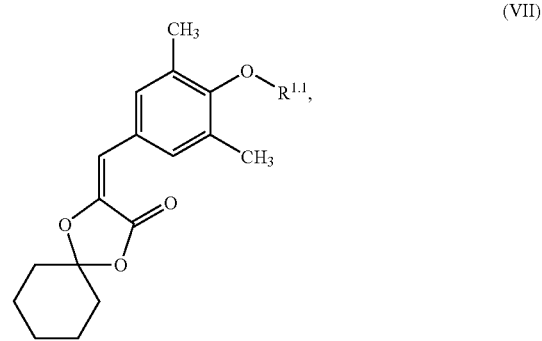

(VII)

thus obtained wherein $R^{1.1}$ is as hereinbefore defined, is optionally recrystallised from a polar solvent;

(c) a compound of general formula VII obtained under (b) is dissolved in a solvent and combined with a strong inorganic base;

(d) a compound of general formula VIII

(VIII)

formed as an intermediate under (c), wherein $R^{1.1}$ is as hereinbefore defined, is reduced in the presence of a base and a reducing agent to form a compound of general formula IX

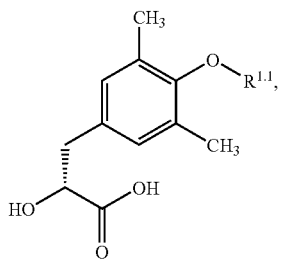
(IX)

wherein $R^{1.1}$ is as hereinbefore defined; and (e) a compound of general formula III wherein X denotes a metal atom selected from among lithium, sodium and potassium, preferably sodium, is isolated by the addition of lithium hydroxide, sodium hydroxide solution or potassium hydroxide solution, preferably sodium hydroxide solution.

In the reaction in step (a) preferably 1.0 equivalents of (diethoxyphosphinyl)-hydroxyacetic acid are reacted with 2.0 to 2.5 equivalents of cyclohexane-dimethylketal. The non-polar aprotic solvent may be selected from among toluene, o-xylene, m-xylene and p-xylene as well as corresponding mixtures of these solvents. Preferably, 1.0 to 3.0 mL solvent/mmol (diethoxyphosphinyl)-hydroxyacetic acid are used.

The acid used in step (a) may preferably be selected from among p-toluenesulphonic acid, methanesulphonic acid, sulphuric acid and benzenesulphonic acid.

The reaction in step (b) is preferably carried out in a solvent which is selected from among tetrahydrofuran, tert.butylmethylether, dioxane, mono-, di-, tri- and polyethyleneglycol ether. The strong base used in the reaction may be selected from among 1,4-diazabicyclo[2,2,2]octane (DABCO), potassium tert.butoxide, tetramethylguanidine and 1,8-diazabicyclo[5,4,1]undec-7-ene (DBU).

If the compounds of general formula VII are crystalline, they may subsequently be recrystallised from a polar solvent which is selected from among methanol, ethanol, propanol, isopropanol and n-propanol. According to the invention methanol is preferably used for the recrystallisation.

The reaction described under step (c) hereinbefore is preferably carried out in methanol, ethanol, propanol, isopropanol or tetrahydrofuran or in a mixture of these solvents.

The strong inorganic base may be selected from among lithium hydroxide, potassium hydroxide, sodium hydroxide and caesium hydroxide.

The base mentioned under step (d) hereinbefore is selected from among triethylamine, diisopropylethylamine and pyridine.

The reducing agent also described under step (d) may be selected from among β-chlorodiisopinocampheylboran, Alpine-borane and methyl-CBS-oxazaborolidine.

In a fifth aspect the present invention relates to the compounds of general formula IV

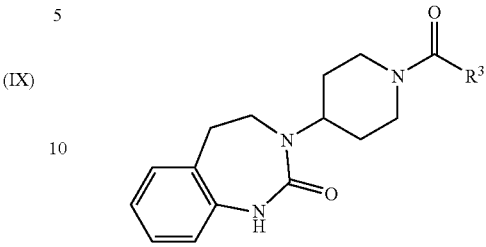
(IV)

wherein $R^3$ denotes an imidazole or triazole group, preferably an imidazole group, which is attached via a nitrogen atom.

A preferred fifth object encompasses the following compound of general formula IVa:

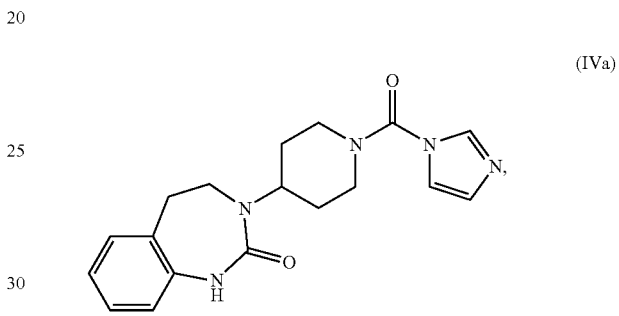
(IVa)

which is obtained in crystalline form and is characterised by a high degree of stability.

The crystalline compound of formula IVa is characterised by a characteristic melting point of T=218±3° C. The value stated was determined by Differential Scanning Calorimetry (DSC: evaluated by onset, heating rate: 10° C./min) (DSC 821 of Mettler Toledo).

In a sixth aspect the present invention relates to a process for preparing compounds of general formula IV

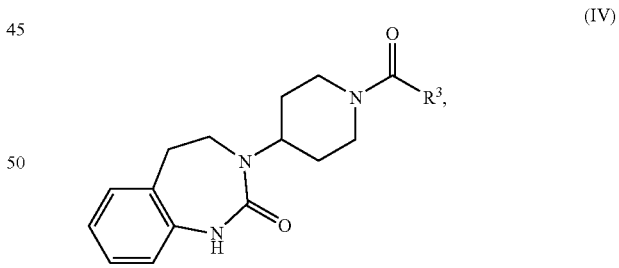
(IV)

wherein $R^3$ denotes an imidazole or triazole group, preferably an imidazole group, which is attached via a nitrogen atom, characterised in that (a) carbonyldiimidazole or carbonylditriazole, preferably carbonyldiimidazole, is dissolved in a polar aprotic solvent and is reacted at elevated temperature with 1,3,4,5-tetrahydro-3-(4-piperidinyl)-2H-1,3-benzodiazepin-2-one; and (b) a crude product formed in step (a) is crystallised by the addition of another polar aprotic solvent, if $R^3$ denotes an imidazole group.

The solvent mentioned under step (a) hereinbefore may be selected from among acetone, acetonitrile, tert.butylmethylether, N,N-dimethylacetamide, dimethylformamide, dimethylsulphoxide, pyridine and N-methylpyrrolidone.

The polar aprotic solvent mentioned under step (b) hereinbefore may be selected from among tert.butylmethylether and dimethylformamide.

A seventh embodiment of the present invention relates to a process for preparing compounds of general formula V

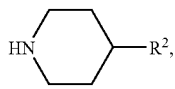
(V)

wherein
$R^2$ denotes a secondary amine —$NR^{2.1}R^{2.2}$, wherein
$R^{2.1}$ and $R^{2.2}$ independently of one another may be selected from among $C_{1-3}$-alkyl and benzyl, or
the group —$NR^{2.1}R^{2.2}$ together forms a cyclic amine which may be selected from among morpholin-4-yl, 1-methylpiperazin-4-yl, 1-benzylpiperazin-4-yl, 1-($C_{1-3}$-alkylcarbonyl)-piperazin-4-yl, 1-(tert.butyloxycarbonyl)-piperazin-4-yl, 1-(benzyloxycarbonyl)-piperazin-4-yl, piperidin-1-yl and pyrrolidin-1-yl, preferably morpholin-4-yl,
comprising the steps of:
(a) reaction of 1-benzylpiperidone with an amine of general formula X

(X)

wherein $R^{2.1}$ and $R^{2.2}$ are defined as hereinbefore, in a solvent and in the presence of an acid;
(b) reduction in the presence of a reducing agent and isolation of the resulting product of general formula XI

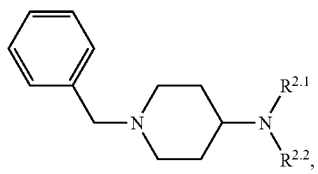
(XI)

wherein $R^{2.1}$ and $R^{2.2}$ are defined as hereinbefore and
(c) removal of the benzyl protecting group from a compound of general formula XI obtained under (b) in a polar solvent and in the presence of a reducing agent and
(d) isolation of a compound of general formula XII obtained under (c)

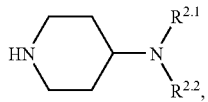
(XII)

wherein $R^{2.1}$ and $R^{2.2}$ are defined as hereinbefore.

In the reaction in step (a) preferably 1.0 equivalents of 1-benzylpiperidone are reacted with 1.0 to 1.5 equivalents, preferably 1.1 to 1.2 equivalents, of an amine of general formula X.

The solvent used may be selected from among 2-methyltetrahydrofuran, toluene, tetrahydrofuran, tert.butylmethylether, dioxane, mono-, di-, tri- and polyethyleneglycol ether, while tetrahydrofuran is preferably used. Preferably, 2.0 to 5.0 mL of solvent are used per mmol of 1-benzylpiperidone, particularly preferably 2.0 to 3.0 mL of solvent are used per mmol of 1-benzylpiperidone. The acid used may preferably be selected from among p-toluenesulphonic acid, methanesulphonic acid, sulphuric acid and benzenesulphonic acid; preferably, p-toluenesulphonic acid is used.

The reduction in step (b) is carried out in the presence of a reducing agent which may be selected from among sodium triacetoxyborohydride and sodium borohydride; preferably, sodium triacetoxyborohydride is used. The reducing agent may be added in an amount of from 1.0 to 3.0 equivalents, preferably from 1.0 to 2.0 equivalents, particularly preferably 1.5 equivalents, based in each case on the amount of 1-benzylpiperidone used.

The cleaving of a benzyl protecting group described under step (c) from a compound of general formula XI may be carried out in a polar solvent such as, for example, methanol, ethanol, water, acetone, tetrahydrofuran, dimethylformamide or propanol. The solvent is added in an amount of from 1.5 to 5.0 mL/mmol of compound of general formula XI used, preferably from 2.0 to 4.0 mL/mmol of compound of general formula XI used, particularly preferably 2.5 mL/mmol of compound of general formula XI used.

The reduction is carried out in a pressurised reactor. The hydrogenating agent used may be Pd/C or Pd(OH)$_2$, for example. Advantageous conditions for hydrogenation are temperatures from 40 to 80° C. and an excess hydrogen pressure of not more than 3 bar.

The isolation of a compound of general formula XII may be carried out by crystallisation, for example.

TERMS AND DEFINITIONS USED

Within the scope of this application, in the definition of possible substituents, these may also be represented in the form of a structural formula. If present, an asterisk (*) in the structural formula of the substituent is to be understood as being the linking point to the rest of the molecule.

The subject-matter of this invention also includes the compounds according to the invention, including the salts thereof, wherein one or more hydrogen atoms, for example one, two, three, four or five hydrogen atoms, are replaced by deuterium.

By the term "secondary amine" is meant an amino group of general formula —$NR^{2.1}R^{2.2}$, wherein the groups $R^{2.1}$ and $R^{2.2}$ independently of one another may be selected from among $C_{1-3}$-alkyl and benzyl, or the group —$NR^{2.1}R^{2.2}$ together forms a cyclic amine which may be selected from among morpholin-4-yl, 1-methylpiperazin-4-yl, 1-benzylpiperazin-4-yl, 1-$C_{1-3}$-alkylcarbonyl-piperazin-4-yl, 1-tert.butyloxycarbonyl-piperazin-4-yl, 1-benzyloxycarbonyl-piperazin-4-yl, piperidin-1-yl and pyrrolidin-1-yl.

Examples include:

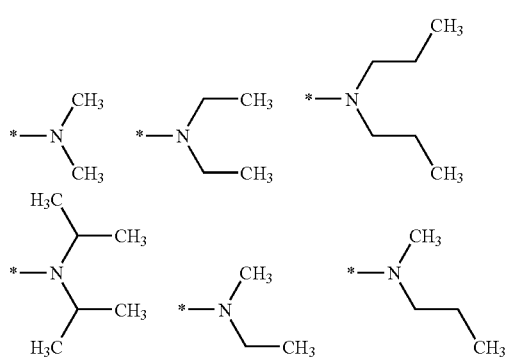

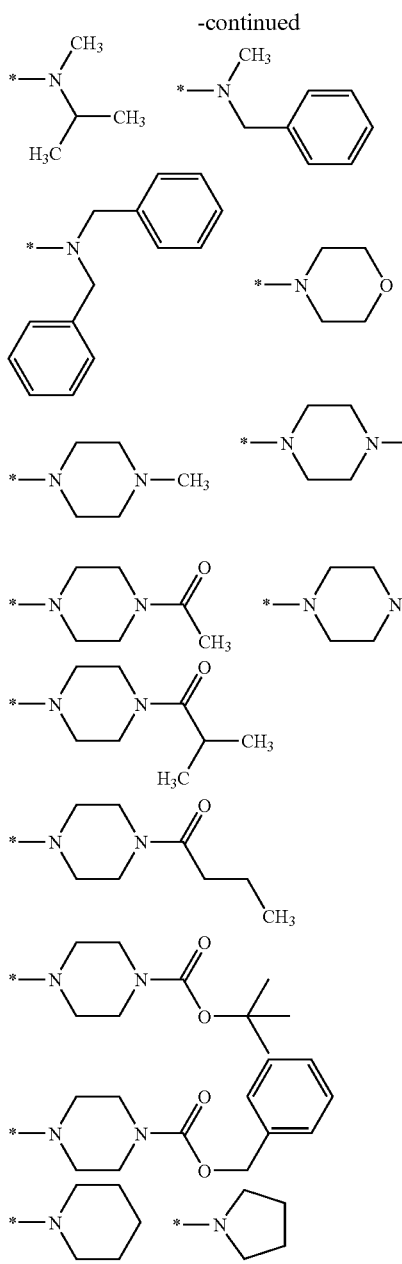

By the term "$C_{1-3}$-alkyl" (including those which are part of other groups) are meant branched and unbranched alkyl groups with 1 to 3 carbon atoms. Examples include: methyl, ethyl, n-propyl or iso-propyl. The following abbreviations may optionally also be used for the above-mentioned groups: Me, Et, n-Pr, i-Pr, etc.

The compounds of general formula I may contain basic groups such as e.g. amino functions. They may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid or citric acid.

The invention relates to the respective compounds optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example tartaric acid, fumaric acid, diglycolic acid or methanesulphonic acid.

EXPERIMENTAL SECTION

Example 1

Diethyl (3-oxo-1,4-dioxaspiro[4.5]dec-2-yl)-phosphonate (C)

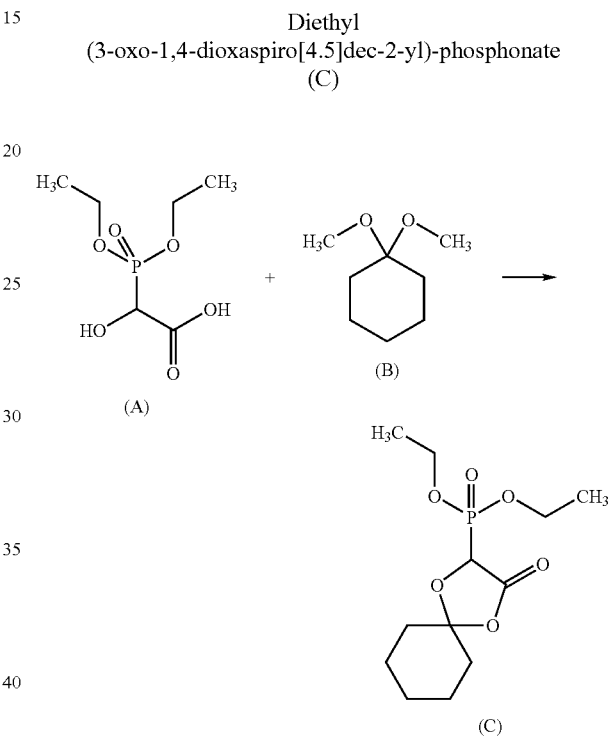

In a reaction vessel with a descending condenser, 50 g (0.236 Mol) (diethoxyphosphinyl)-hydroxyacetic acid (A) and 240 mL toluene are mixed at ambient temperature and then heated to 110° C. When the boiling temperature of toluene is reached, a mixture of 71.7 mL (0.471 Mol) cyclohexane-dimethylketal (B) and 10 mL toluene are slowly added dropwise, while the azeotrope of toluene and methanol is distilled off. After the addition has ended the reaction mixture is refluxed for 90 minutes. Any solvent distilled off is replaced by the addition of 50 mL toluene. In order to achieve total conversion, a further 10 mL (0.066 Mol) of cyclohexane-dimethylketal (B) are added dropwise. The mixture is heated to a 110° C. for another hour and the solvent distilled off is replaced by the addition of another 100 mL toluene. After the addition of another 120 mL toluene the solvent is distilled off in vacuo. The residue is taken up in 200 mL tert.butyl-methylether and successively extracted twice with 200 mL of 10% potassium carbonate solution, once with 250 mL of 30% sodium bisulphite solution and once with 150 mL of 30% sodium bisulphite solution. After subsequent extraction with 40 mL saturated saline solution the organic phase is dried and evaporated down.

Yield: 59 g (86% of theory)

Example 2

(3E)-3-[[3,5-dimethyl-4-(phenylmethoxy)phenyl]methylene]-1,4-dioxaspiro[4.5]decan-2-one (E)

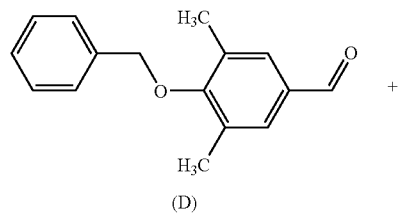

(D)

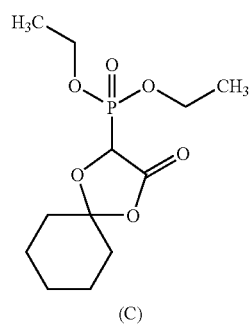

(C)

→

(E)

4.2 g lithium chloride (0.1 Mol), 20.0 g (83.2 mmol) of 4-benzyloxy-3,5-dimethylbenzaldehyde (D) and 31.62 g (108.2 mmol) of diethyl (3-oxo-1,4-dioxaspiro[4.5]dec-2-yl)-phosphonate (C) are suspended in 130 mL tetrahydrofuran and cooled to −20° C. At this temperature 12.5 mL (0.1 Mol) tetramethylguanidine are added dropwise. After the addition has ended the suspension formed is heated to ambient temperature and stirred for 1 hour. After the addition of 190 mL tert.butyl-methylether the organic phase is washed with 150 mL water and 30 mL saturated saline solution, dried and evaporated down. The resulting yellow oil is taken up in 145 mL methanol and stirred intensively for 1 hour at −10° C., during which time a white solid is formed. The solid formed is suction filtered, washed twice with 20 mL methanol/water (1:1) and dried at 45° C.

Yield: 26.0 g (86% of theory)

Example 3

(αR)-α-Hydroxy-3,5-dimethyl-4-(phenylmethoxy)-phenylpropionic acid-monosodium salt (G)

(E) →NaOH (F) →1. DIP-Cl 2. NaOH (G)

10.0 g (26.4 mmol) of (3E)-3-[[3,5-dimethyl-4-(phenylmethoxy)phenyl]methylene]-1,4-dioxaspiro[4.5]decan-2-one (E) are dissolved in 90 mL tetrahydrofuran and 10 mL ethanol. At 10° C., 26.4 mL (53 mmol) of 2N sodium hydroxide solution are added dropwise. The reaction mixture is heated to ambient temperature for 1 hour. After the addition of 90 mL toluene the resulting 2-phase mixture is stirred for 5 minutes. After separation of the phases the aqueous phase is combined with 30 mL of 2N hydrochloric acid, combined with 13 g sodium chloride and extracted with 40 mL 2-methyl-tetrahydrofuran. The organic phase is dried on sodium sulphate. The drying agent is filtered off and the remaining substance is washed with 10 mL 2-methyl-tetrahydrofuran. The combined organic phases are combined with another 50 mL of 2-methyl-tetrahydrofuran.

The solution of (2E)-3-[3,5-dimethyl-4-(phenylmethoxy)phenyl]-2-hydroxy-2-propenoic acid (F) thus obtained is combined at 0° C. with 4.4 mL (32 mmol) of triethylamine. After cooling to −20° C., 16.9 mL of β-chlorodiisopinocampheylboran (65% solution in hexane) are added dropwise. After 2 hours at −20 to −30° C., 30 mL 2N hydrochloric acid and 50 mL ethyl acetate are added. After extraction and separation of the phases the organic phase is dried and evaporated down. The residue is dissolved in 150 mL tert.butyl-methyl-ether and cooled to 0° C. After the addition of 6.6 mL of 4N sodium hydroxide solution the suspension formed is stirred for 1 hour and filtered. The isolated solid is dried.

| Yield: | 6.6 g (77% of theory) |
|---|---|
| ee value: | 78% |
| chemical purity (HPLC): | 97.5% |
| melting point: | 237° C. |

Example 4

1-(1H-imidazol-1-yl-carbonyl)-4-(1,2,4,5-tetrahydro-2-oxo-3H-1,3-benzodiazepin-3-yl)-piperidine (J)

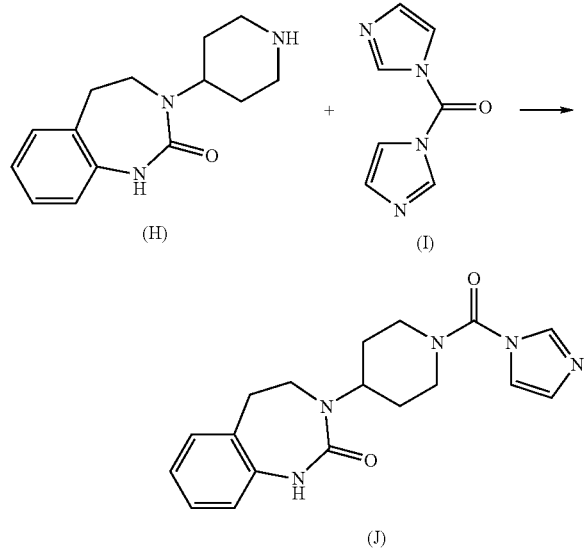

10 g (44.8 mmol) of carbonyldiimidazole (I) are in 40 mL dimethylformamide at 40 to 50° C. dissolved. Then 10.0 g (40.8 mmol) of 1,3,4,5-tetrahydro-3-(4-piperidinyl)-2H-1,3-benzodiazepin-2-one (H) are added batchwise. The suspension formed is liquefied by the addition of 40 mL tert.butyl-methylether and cooled to ambient temperature. After the addition of another 40 mL tert.butyl-methylether the suspension is filtered, the isolated solid is washed with 100 mL tert.butyl-methylether and dried.

| Yield: | 12.9 g (93% of theory) |
|---|---|
| chemical purity (HPLC): | 98.2% |
| melting point: | 218° C. |

Example 5

Ethyl (1R)-4-(1,2,4,5-tetrahydro-2-oxo-3H-1,3-benzodiazepin-3-yl)-1-carboxy-2-[3,5-dimethyl-4-(phenylmethoxy)phenyl]-1-piperidinecarboxylate (K)

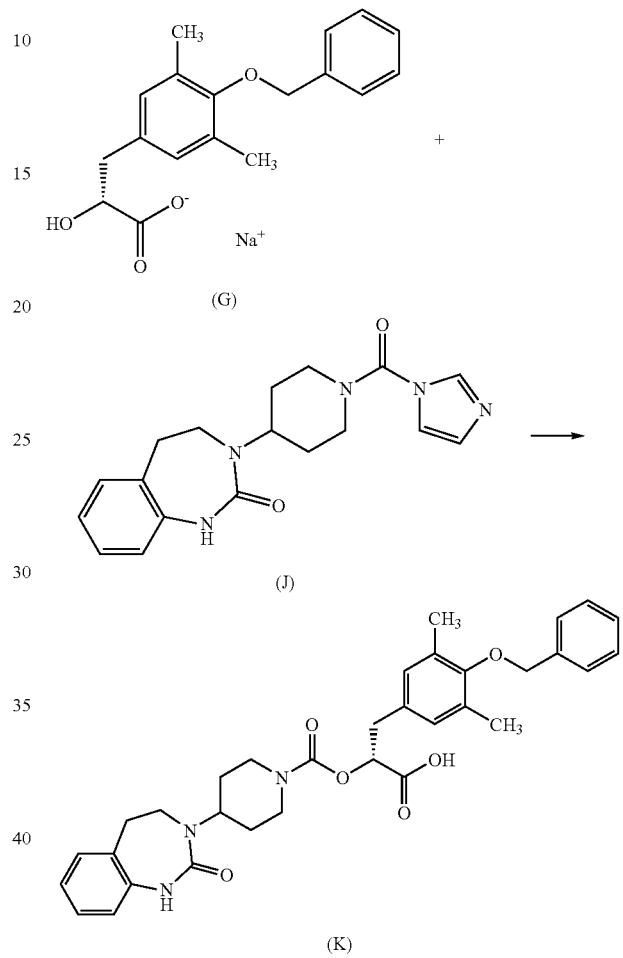

10.527 g (31.8 mmol) of (αR)-α-hydroxy-3,5-dimethyl-4-(phenylmethoxy)-phenylpropionic acid-monosodium salt (G) and 11.88 g (35 mmol) of 1-(1H-imidazol-1-yl-carbonyl)-4-(1,2,4,5-tetrahydro-2-oxo-3H-1,3-benzodiazepin-3-yl)-piperidine (J) are suspended in 50 mL tert-butanol and tetrahydrofuran at ambient temperature. The suspension is heated to 70 to 75° C., while 20 mL solvent are distilled off. Then at 65° C. a 24% solution of potassium-tert-butoxide (16.4 g, 35 mmol) in tetrahydrofuran is added dropwise. After 30 minutes at 70° C. a further 1.2 g (3.5 mmol) of 1-(1H-imidazol-1-ylcarbonyl)-4-(1,2,4,5-tetrahydro-2-oxo-3H-1, 3-benzodiazepin-3-yl)-piperidine are added. After another hour the reaction mixture is cooled to 45° C. and combined with 60 mL 2 N hydrochloric acid while cooling with ice. After the addition of 40 mL ethyl acetate and subsequent extraction the phases are separated. The organic phase is washed with 20 mL saturated saline solution and evaporated down. The residue is taken up in 180 mL n-butyl acetate and 10 mL water and refluxed for 1 hour. After cooling to ambient temperature the suspension is stirred for 12 hours and filtered. The residue is washed with 20 mL n-butyl acetate and dried.

| Yield: | 15.8 g (87% of theory) |
| ee value: | 80% |
| chemical purity (HPLC): | 97.3% |

The ee value can be increased to 95% by recrystallisation from isopropanol/water (20:1).

Example 6

4-[1-(phenylmethyl)-4-piperidinyl]-morpholine (N)

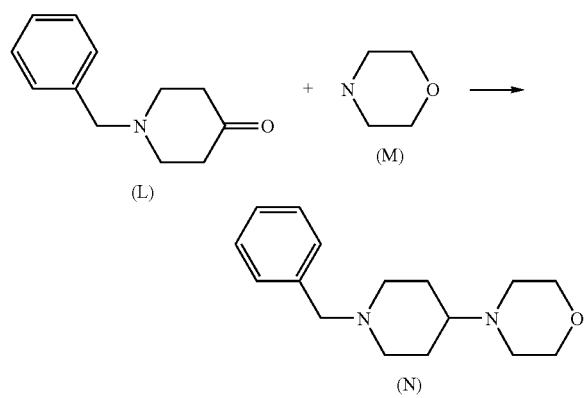

30 mL (0.162 Mol) 1-benzylpiperidone (L) and 16.1 mL (0.185 Mol) morpholine (M) are dissolved in 407 mL tetrahydrofuran at ambient temperature. While cooling, 1.0 g (5 mmol) of p-toluenesulphonic acid and 14.6 mL glacial acetic acid are added, whereupon a jelly-like precipitate is formed. 52.19 g (0.246 Mol) sodium triacetoxyborohydride are added while cooling with ice, during which time the reaction temperature rises to 30° C. After 4 hours at 20° C., 90 mL water are added dropwise. After another 30 minutes, 280 mL of 17% potassium carbonate solution are added. The mixture is stirred intensively, while gas is observed to be given off. After separation of the phases the organic phase is dried and evaporated down.

Yield: 33.0 g (78% of theory)

Example 7

4-(4-piperidinyl)-morpholine (O)

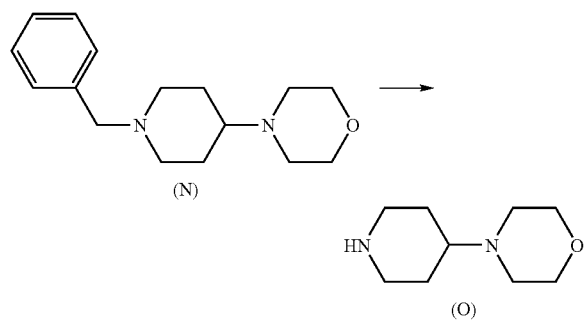

41.59 g (0.16 Mol) 4-[1-(phenylmethyl)-4-piperidinyl]-morpholine (N) are dissolved in 400 mL methanol, combined with 5.2 g palladium on activated charcoal (10%) and hydrogenated for 18 hours at ambient temperature with 50 psi hydrogen. The catalyst is filtered off and the filtrate is evaporated down. A colourless oil remains, which crystallises after a short time.

Yield: 25.29 g (93% of theory)

Example 8

2-oxoethyl (1R)-4-(1,2,4,5-tetrahydro-2-oxo-3H-1,3-benzodiazepin-3-yl)-1-[[3,5-dimethyl-4-(phenylmethoxy)phenyl]methyl]-2-[4-(4-morpholinyl)-1-piperidinyl]-1-piperidinecarboxylate (P)

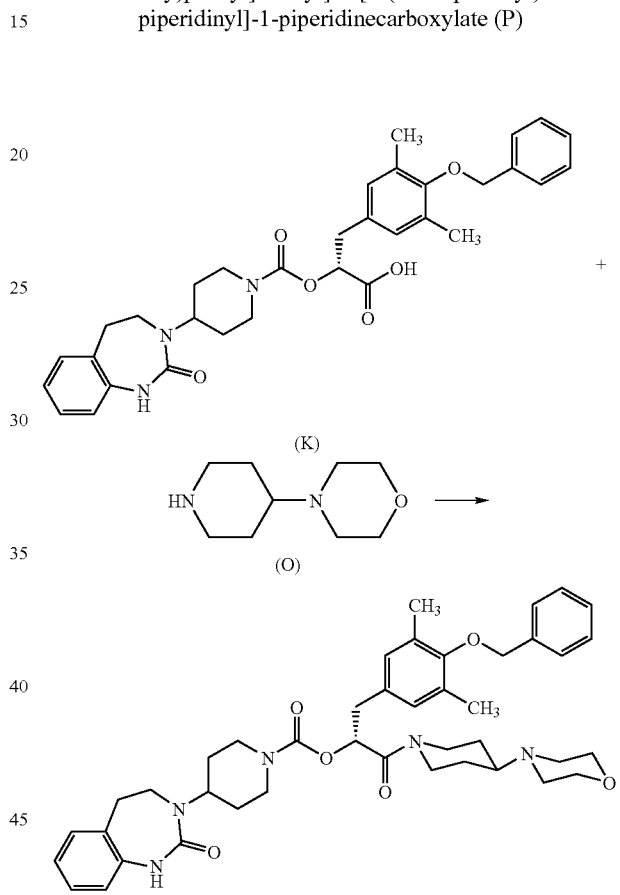

27.5 g (48.1 mmol) of ethyl (1R)-4-(1,2,4,5-tetrahydro-2-oxo-3H-1,3-benzodiazepin-3-yl)-1-carboxy-2-[3,5-dimethyl-4-(phenylmethoxy)phenyl]-1-piperidinecarboxylate (K) and 9.75 g (57.3 mmol) of 4-(4-piperidinyl)-morpholine (O) are dissolved at ambient temperature in 200 mL tetrahydrofuran. The solution is cooled to 0 to 10° C. and combined with 16.1 mL (115.4 mmol) of triethylamine. Then 37.2 mL (62.5 mmol) of propanephosphonic anhydride (50% solution in ethyl acetate) are added dropwise at this temperature. After one hour the reaction mixture is heated to ambient temperature. After the addition of 175 mL ethyl acetate the organic solution is washed with 70 mL of 10% potassium carbonate solution and with 70 mL saturated sodium chloride solution, dried and evaporated down.

| Yield: | 32.9 g (94% of theory) |
| --- | --- |
| chemical purity (HPLC): | 90.9% |
| ee value: | 99.7% |

Example 9

2-oxoethyl (1R)-4-(1,2,4,5-tetrahydro-2-oxo-3H-1,3-benzodiazepin-3-yl)-1-[[3,5-dimethyl-4-hydroxy)phenyl]methyl]-2-[4-(4-morpholinyl)-1-piperidinyl]-1-piperidinecarboxylate (Q)

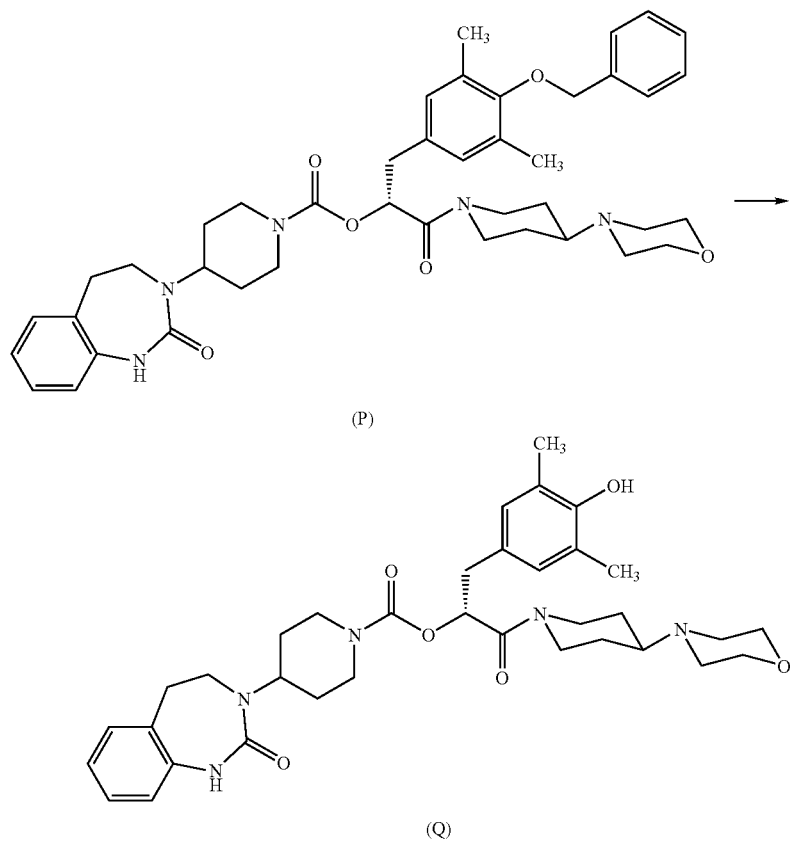

31.1 g (43 mmol) of 2-oxoethyl (1R)-4-(1,2,4,5-tetrahydro-2-oxo-3H-1,3-benzodiazepin-3-yl)-1-[[3,5-dimethyl-4-(phenylmethoxy)phenyl]methyl]-2-[4-(4-morpholinyl)-1-piperidinyl]-1-piperidinecarboxylate (P) are dissolved in 250 mL methanol and hydrogenated with 1.56 g palladium on activated charcoal (10%) at 50° C. After the uptake of hydrogen has ended the catalyst is filtered off and washed with methanol. The filtrate is evaporated down with the addition of ethanol.

| Yield: | 27.4 g |
| --- | --- |
| chemical purity (HPLC): | 92.4% |
| ee value: | 98.8% |

What is claimed is:

1. A compound of the formula III

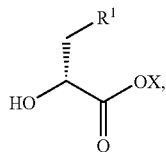

wherein $R^1$ denotes a group

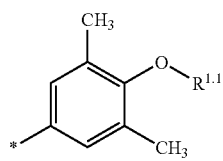

wherein $R^{1.1}$ denotes H, $C_{1-3}$-alkyl, C(O)—O-benzyl, C(O)—O-tert.butyl or benzyl, and X denotes a hydrogen atom or a metal atom selected from the group consisting of lithium, sodium and potassium.

2. A compound according to claim 1 selected from the group consisting of:

(1)

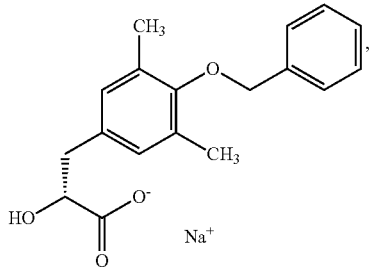

(2)

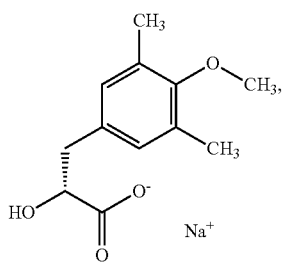

(3)

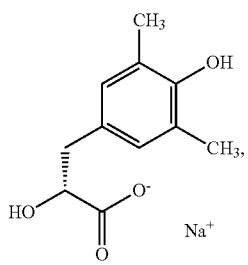

(4)

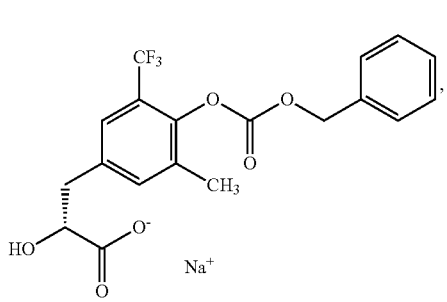

and (5)

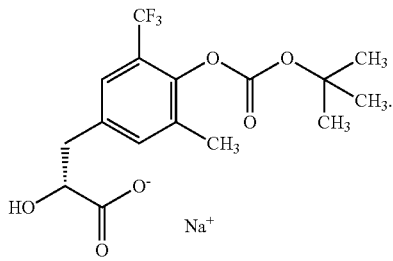

3. The compound according to claim 1 of the formula (IIIa)

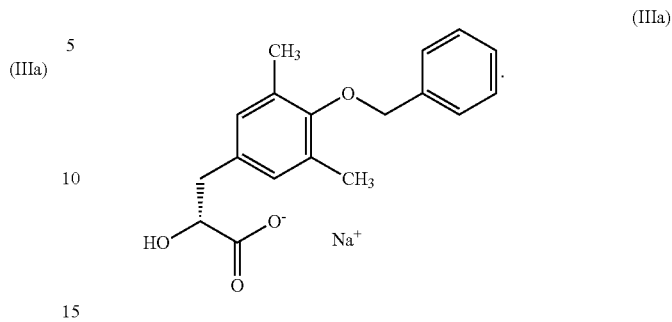

4. A process for preparing a compound of the formula III (III)

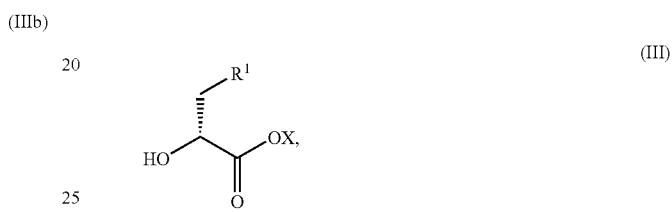

wherein
$R^1$ denotes a group

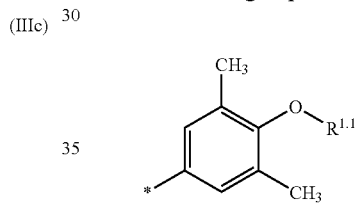

wherein
$R^{1.1}$ denotes H, $C_{1-3}$-alkyl, C(O)—O-benzyl, C(O)—O-tert.butyl or benzyl,
X denotes a hydrogen atom or a metal atom selected from the group consisting of lithium, sodium and potassium,
Wherein,
(a) (diethoxyphosphinyl)-hydroxyacetic acid is reacted with cyclohexane dimethylketal and optionally in the presence of an acid in a non-polar aprotic solvent and the diethyl (3-oxo-1,4-dioxaspiro[4.5]dec-2-yl)-phosphonate is obtained by azeotropic distillation of the methanol released;
(b) the diethyl (3-oxo-1,4-dioxaspiro[4.5]dec-2-yl)-phosphonate obtained under (a) is reacted in the presence of lithium chloride and a strong base with a compound of the formula VI (VI)

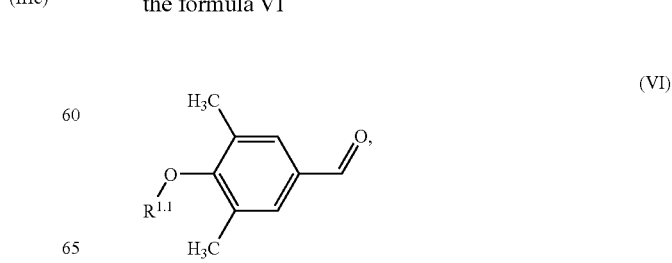

wherein $R^{1.1}$ is defined as above, and a compound of the formula VII

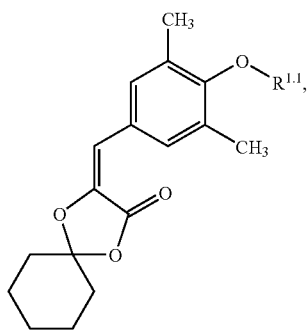

(VII)

thus obtained wherein $R^{1.1}$ is defined above, is optionally recrystallised from a polar solvent;
(c) a compound of the formula VII obtained under (b) is dissolved in a solvent and combined with a strong inorganic base;
(d) a compound of the formula VIII

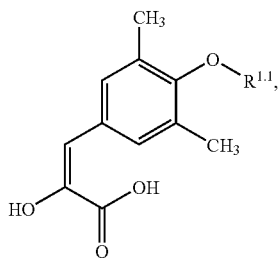

(VIII)

formed as an intermediate under (c), wherein $R^{1.1}$ is defined as above, is reduced in the presence of a base and a reducing agent to form a compound of the formula IX

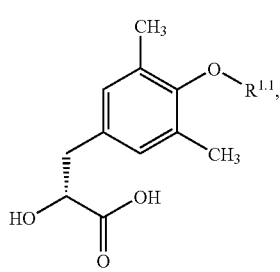

(IX)

wherein $R^{1.1}$ is defined as above; and
(e) a compound of the formula III wherein X denotes a metal atom selected from the group consisting of lithium, sodium and potassium, is isolated by the addition of lithium hydroxide, sodium hydroxide solution or potassium hydroxide.

5. The process according to claim 4, wherein, in step (a), 1.0 equivalents of (diethoxyphosphinyl)-hydroxyacetic acid are reacted with 2.0 to 2.5 equivalents of cyclohexanedimethylketal.

6. The process according to claim 4, wherein $R^{1.1}$ denotes benzyl.

* * * * *